(12) United States Patent
Zhao et al.

(10) Patent No.: US 12,031,119 B2
(45) Date of Patent: Jul. 9, 2024

(54) METHOD FOR ENRICHING AND SEPARATING ANAEROBIC FIBER-DEGRADING BACTERIUM ON THE BASIS OF CELLULOSIC MAGNETIC NANOPARTICLES

(71) Applicant: INSTITUTE OF ANIMAL SCIENCES, CHINESE ACADEMY OF AGRICULTURAL SCIENCES, Beijing (CN)

(72) Inventors: Shengguo Zhao, Beijing (CN); Jiaqi Wang, Beijing (CN); Nan Zheng, Beijing (CN); Lei Xing, Beijing (CN); Yangdong Zhang, Beijing (CN); Songli Li, Beijing (CN)

(73) Assignee: INSTITUTE OF ANIMAL SCIENCES, CHINESE ACADEMY OF AGRICULTURAL SCIENCES, Beijing (CN)

( * ) Notice: Subject to any disclaimer, the term of this patent is extended or adjusted under 35 U.S.C. 154(b) by 745 days.

(21) Appl. No.: 17/058,991

(22) PCT Filed: Jul. 12, 2018

(86) PCT No.: PCT/CN2018/095478
§ 371 (c)(1),
(2) Date: Nov. 25, 2020

(87) PCT Pub. No.: WO2019/223081
PCT Pub. Date: Nov. 28, 2019

(65) Prior Publication Data
US 2021/0214674 A1    Jul. 15, 2021

(30) Foreign Application Priority Data
May 25, 2018    (CN) .......................... 201810515019.8

(51) Int. Cl.
| | | |
|---|---|---|
| *C12N 1/02* | (2006.01) |
| *B01J 20/06* | (2006.01) |
| *B01J 20/24* | (2006.01) |
| *B01J 20/28* | (2006.01) |
| *B01J 20/30* | (2006.01) |
| *C12N 1/20* | (2006.01) |

(52) U.S. Cl.
CPC ................ *C12N 1/02* (2013.01); *B01J 20/06* (2013.01); *B01J 20/24* (2013.01); *B01J 20/28009* (2013.01); *B01J 20/30* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 2010/0203313 A1 | 8/2010 | Olsson et al. | |
| 2015/0357099 A1* | 12/2015 | Galland | C01G 49/0072 428/389 |
| 2017/0369924 A1* | 12/2017 | Pilarski | C12Q 1/6806 |

FOREIGN PATENT DOCUMENTS

| | | | |
|---|---|---|---|
| CN | 1597929 A | | 3/2005 |
| CN | 101789295 A | | 7/2010 |
| CN | 101979633 A | | 2/2011 |
| CN | 102424812 A | * | 4/2012 |
| CN | 102424812 A | | 4/2012 |
| CN | 102533716 A | | 7/2012 |
| CN | 107354469 A | | 11/2017 |

* cited by examiner

*Primary Examiner* — Nghi V Nguyen
(74) *Attorney, Agent, or Firm* — NKL Law; Allen Xue

(57) ABSTRACT

In a method for enriching and separating an anaerobic fiber-degrading bacterium on the basis of cellulosic magnetic nanoparticles, the cellulosic magnetic nanoparticles are prepared by coating cellulose on the surface of a magnetic nanomaterial. Bacteria attach to the cellulosic magnetic nanoparticles. Anaerobic fiber-degrading bacteria degrade the cellulose and then detach from the cellulosic magnetic nanoparticles, and the anaerobic fiber-degrading bacteria are obtained by means of separation using a magnet. The magnetic nano-separation technology can be used as a new technology to efficiently separate anaerobic fiber-degrading bacteria.

12 Claims, 3 Drawing Sheets

METHOD FOR ENRICHING AND SEPARATING ANAEROBIC FIBER-DEGRADING BACTERIUM ON THE BASIS OF CELLULOSIC MAGNETIC NANOPARTICLES

FIELD OF THE INVENTION

The present invention belongs to the field of biotechnology, and specifically relates to a method for enriching and isolating anaerobic cellulolytic (fiber-degrading) bacteria based on cellulose magnetic nanoparticles.

BACKGROUND

Cellulose is an essential nutrient for human body or animals, and cellulose degradation is accomplished by anaerobic cellulolytic bacteria present in gastrointestinal tracts. Previous studies have found that the anaerobic cellulolytic bacteria present in gastrointestinal tracts have high diversity and 90% or more of them have not been isolated and cultivated. Conventional methods for microbial isolation and cultivation mainly include dilution culture methods, microbial co-cultures, etc. However, these methods have disadvantages, such as low isolation efficiency, complicated operations, expensive equipments, or lack of group interactions, so that new anaerobic cellulolytic bacteria with specific functions are difficult to be isolated.

SUMMARY OF THE INVENTION

To overcome the disadvantages and deficiencies of the prior arts, a primary object of the present invention is to provide a method for enriching and isolating anaerobic cellulolytic bacteria based on cellulose magnetic nanoparticles.

Another object of the present invention is to provide a method of preparation of cellulose magnetic nanoparticles used in the method.

Another object of the present invention is to provide cellulose magnetic nanoparticles prepared by the above-mentioned method of preparation.

Another object of the present invention is to provide use of the above-mentioned cellulose magnetic nanoparticles, which may used for enriching and isolating anaerobic cellulolytic bacteria.

The objects of the present invention are realized by the following technical solutions:

A method for enriching and isolating anaerobic cellulolytic bacteria based on cellulose magnetic nanoparticles, the method including the following steps:
  adding bacteria into a solution containing cellulose magnetic nanoparticles, the bacteria containing anaerobic cellulolytic bacteria; mixing and incubating; and then carrying out isolation using magnetic attraction to obtain anaerobic cellulolytic bacteria;
  wherein, the cellulose magnetic nanoparticles include magnetic nanoparticles and cellulose layers coated on surfaces of the particles.

According to the present invention, the magnetic nanoparticles are selected from $Fe_3O_4$ nanoparticles.

According to the present invention, the average particle size of the magnetic nanoparticles is from 10 nm to 30 nm, such as 18 nm, 20 nm, 22 nm.

According to the present invention, the solution containing cellulose magnetic nanoparticles is formulated by adding cellulose magnetic nanoparticles into an anaerobic diluent.

According to the present invention, the concentration of the cellulose magnetic nanoparticles is from 0.1 mg/ml to 10 mg/ml, such as 8.70 mg/ml, 5.80 mg/ml, 4.35 mg/ml, 1.74 mg/ml, 0.87 mg/ml, 0.44 mg/ml, preferably from 4.35 mg/ml to 10 mg/ml, more preferably 8.70 mg/ml.

According to the present invention, the concentration of the bacteria is $(0.8-1.2)\times10^8$ CFU/mL, preferably $1.0\times10^8$ CFU/mL.

According to the present invention, the duration for mixing may be 5 minutes to 60 hours, preferably from 5 minutes to 15 minutes, such as 5 minutes, 8 minutes, 9 minutes, 10 minutes, 15 minutes.

According to the present invention, the duration for incubation does not exceed 60 hours, and may be from 0 to 60 hours, preferably from 12 hours to 60 hours, such as 12 hours, 24 hours, 48 hours, 60 hours.

According to the present invention, during the mixing and incubation processes, the bacterial adhesion, the cellulose degradation on the surface of the cellulose magnetic nanoparticles by anaerobic cellulolytic bacteria and the dissociation of anaerobic cellulolytic bacteria are realized. Since cellulose has high affinity to bacterial cell walls, the cellulose magnetic nanoparticles can adhere to bacteria. Because the anaerobic cellulolytic bacteria have effects on the cellulose degradation, they can degrade cellulose on the surface of the cellulose magnetic nanoparticles gradually, and the anaerobic cellulolytic bacteria can in turn be dissociated into the liquid environment, wherein the liquid is, for example, selected from an anaerobic diluent.

According to the present invention, the isolation using magnetic attraction is specifically performed by using magnetic attraction, sucking the supernatant and adding with an anaerobic diluent, and adding with an anaerobic diluent after washing. The number of times of the washing may be 1-3 times, such as once, twice, three times.

The present invention also provides a method of preparation of cellulose magnetic nanoparticles used in the above-mentioned method, including:
  (1) dispersing cellulose in an alkaline solution to obtain a cellulose dispersion;
  (2) mixing and reacting magnetic nanoparticles and the above-mentioned cellulose dispersion to obtain cellulose magnetic nanoparticles, the cellulose magnetic nanoparticles including magnetic nanoparticles and cellulose layers coated on surfaces of the particles.

According to the present invention, the concentration of the cellulose magnetic nanoparticles in the mixture system of the magnetic nanoparticles and cellulose dispersion is from 7 mg/ml to 28 mg/ml, preferably from 10 mg/ml to 25 mg/ml, such as about 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml.

According to the present invention, an average particle size of the magnetic nanoparticles is from 10 nm to 30 nm, such as 18 nm, 20 nm, 22 nm.

According to the present invention, the method of preparation of the magnetic nanoparticles includes but is not limited to: ultrasonication of a mixture of $FeCl_2$ and $FeCl_3$ under alkaline conditions to obtain magnetic nanoparticles. Preferably, the base used in the alkaline conditions may be NaOH. Preferably, after the ultrasonication is complete, the steps of magnetic separation and washing are further included; wherein, the duration for being captured by a magnet in the magnetic separation step may be 2-8 minutes, such as 3 minutes, 5 minutes, 7 minutes; the solvent used in the washing step is water, such as ultrapure water; preferably, the washing is carried out until a pH of 7 is reached.

According to the present invention, the alkaline solution in the cellulose dispersion may be sodium hydroxide, urea or a mixed solution of the both.

According to the present invention, in step (2), reaction temperature may be room temperature.

According to the present invention, in step (2), the reaction time may be 5-15 minutes, such as 5 minutes, 8 minutes, 9 minutes, 10 minutes, 15 minutes.

According to the present invention, the method of preparation further includes the steps of magnetic separation and washing of the cellulose magnetic nanoparticles after the reaction is complete. Wherein, the duration for being captured by the magnet in the magnetic separation step may be 2-8 minutes, such as 3 minutes, 5 minutes, 7 minutes. The solvent used in the washing step is water, such as ultrapure water. Preferably, the washing is carried out until a pH of 7 is reached.

In the present invention, the applicant evaluated whether the surface of magnetic nanoparticles was coated with cellulose by using the DNS method, as shown in FIG. 3. FIG. 3 indicates that the surface of magnetic nanoparticles was successfully coated with cellulose.

The present invention also provides cellulose magnetic nanoparticles prepared by the above-mentioned method of preparation, the cellulose magnetic nanoparticles including magnetic nanoparticles and cellulose layers coated on surfaces of the particles.

The present invention also provides use of the above-mentioned cellulose magnetic nanoparticles, the cellulose magnetic nanoparticles may be used for enriching and isolating anaerobic cellulolytic bacteria.

The mechanism of the present invention is shown in FIG. 1. Specifically, the cellulose magnetic nanoparticles of the present invention include magnetic nanoparticles and cellulose layers coated on surfaces of the particles. The cellulose has high affinity to bacterial cell walls, so bacteria may be directionally adhered. After the adhesion is complete, the cellulose on the surface of the cellulose magnetic nanoparticles is gradually degraded using anaerobic cellulolytic bacteria that effect the cellulose degradation, until the anaerobic cellulolytic bacteria detach from the cellulose magnetic nanoparticles, and further are freed into the liquid environment. The anaerobic non-cellulolytic bacteria are still adhered to the surface of the corresponding cellulose magnetic nanoparticles. The magnetic nanoparticles have superparamagnetic properties, and aggregate under the action of an external magnetic field, thus the isolation and enrichment of anaerobic cellulolytic bacteria and anaerobic non-cellulolytic bacteria are achieved.

Comparing with the prior art, the present invention has the following advantages and effects:

(1) The magnetic enrichment method has higher speed, higher isolation efficiency, more convenient operation, lower equipment costs than the enrichment culture method, and saves a lot of time, manpower, materials, and financial resources.

(2) After the surface of magnetic nanoparticles is modified with cellulose, the bacterial capture efficiency is higher. The bacterial binding efficiency of the cellulose magnetic nanoparticles is 90% or more, even 95% or more. When the bacterial concentration is $1.0 \times 10^8$ CFU/mL and a concentration of cellulose magnetic nanoparticles is 8.7 mg/mL, the bacterial binding efficiency achieves 99%. After the bacteria are stably adhered to the cellulose magnetic nanoparticles for 60 h, the stability is 80% or more, even 85% or more, preferably up to 90.24%. Meanwhile, the present invention can achieve the enrichment of various bacteria, rather than being limited to certain bacteria.

(3) Comparing with prior art analysis methods, the methods of the qPCR-based detection and analysis of nucleic acid are faster and more sensitive, and the accuracy of results is also improved.

EXAMPLES

The technical solutions of the present invention will be further illustrated in detail in combination with specific examples. The following examples are intended to give an exemplary description and illustration of the present invention, rather than set any limitation on the scope of protection of the present invention. All technologies implemented based on the above-mentioned content of the present invention fall within the scope of protection of the present invention.

The following experimental methods, unless other specified, are all conventional methods, and the experimental materials used, unless other specified, are all easily obtained from commercial companies.

Example 1

Preparation of an anaerobic medium. The formulation of the medium contains 1 g glucose, 1 g peptone, 6.0 g/L $K_2HPO_4$, 1.21 g/L $CaCl_2$, 6.0 g/L $KH_2PO_4$, 12.0 g/L NaCl, 6.0 g/L $(NH_4)_2SO_4$, 12.5 g/L $MgSO_4 \cdot 7H_2O$, and 0.5 mL heme. The components were prepared according to the above-mentioned formulation and mixed. The mixture was purged with CO2 continuously for 4 hours after boiling. The pH was adjusted to 6.8. The mixture was added with 0.125 g of cysteine hydrochloride, and covered with a stopper quickly. The prepared culture medium was put into an anaerobic glove box, dispensed into anaerobic culture tubes, and autoclaved at a pressure of 121 MPa for 15 minutes to prepare the anaerobic media for further use.

Preparation of an anaerobic diluent. The formulation of the anaerobic diluent contains 6.0 g/L $K_2HPO_4$, 1.21 g/L $CaCl_2$), 6.0 g/L $KH_2PO_4$, 12.0 g/L NaCl, 6.0 g/L $(NH_4)_2SO_4$, 12.5 g/L $MgSO_4 \cdot 7H_2O$, and 0.5 mL heme. The components were prepared according to the above-mentioned formulation and mixed. The mixture was purged with CO2 continuously for 4 hours after boiling. The pH was adjusted to 6.8. The mixture was added with 0.125 g of cysteine hydrochloride, and covered with a stopper quickly.

The prepared culture medium was put into an anaerobic glove box, dispensed into anaerobic culture tubes, and autoclaved at a pressure of 121 MPa for 15 minutes to prepare the anaerobic diluents for further use.

*Streptococcus bovis* (non-cellulolytic bacterium) and Cellulomonas (cellulolytic bacterium) were cultivated. *Streptococcus bovis* and Cellulomonas were strictly anaerobic bacteria. *Streptococcus bovis* and Cellulomonas were inoculated in the anaerobic culture tubes containing the anaerobic media, respectively, and cultivated anaerobically at 37° ° C. for 48 h.

Example 2

Figure 1:
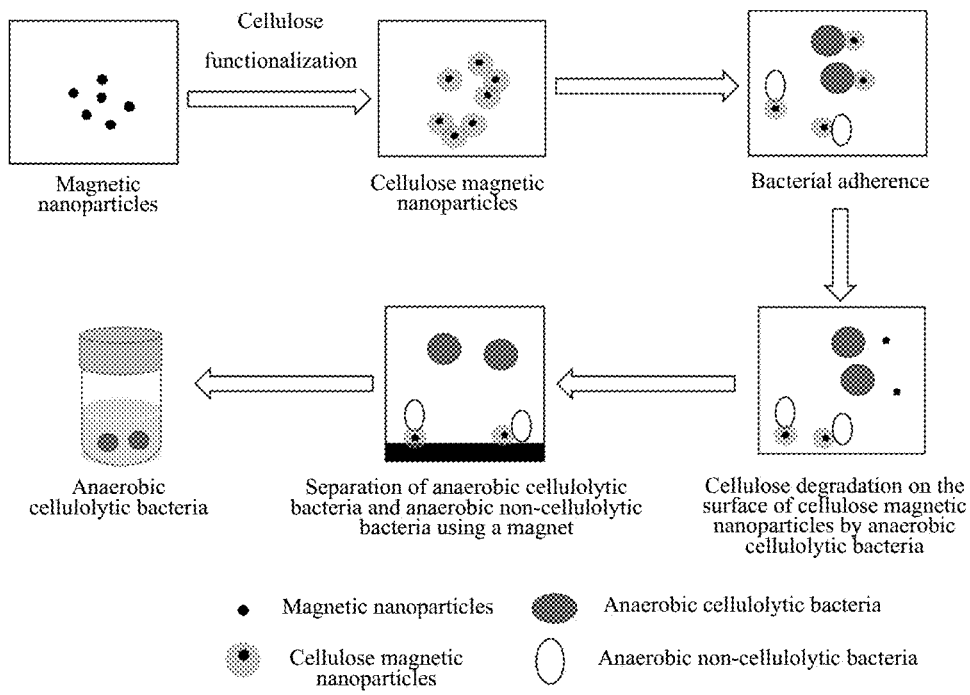
FIG. 1. A schematic diagram of a method for enriching and isolating anaerobic cellulolytic bacteria based on cellulose magnetic nanoparticles.
Figure 2:
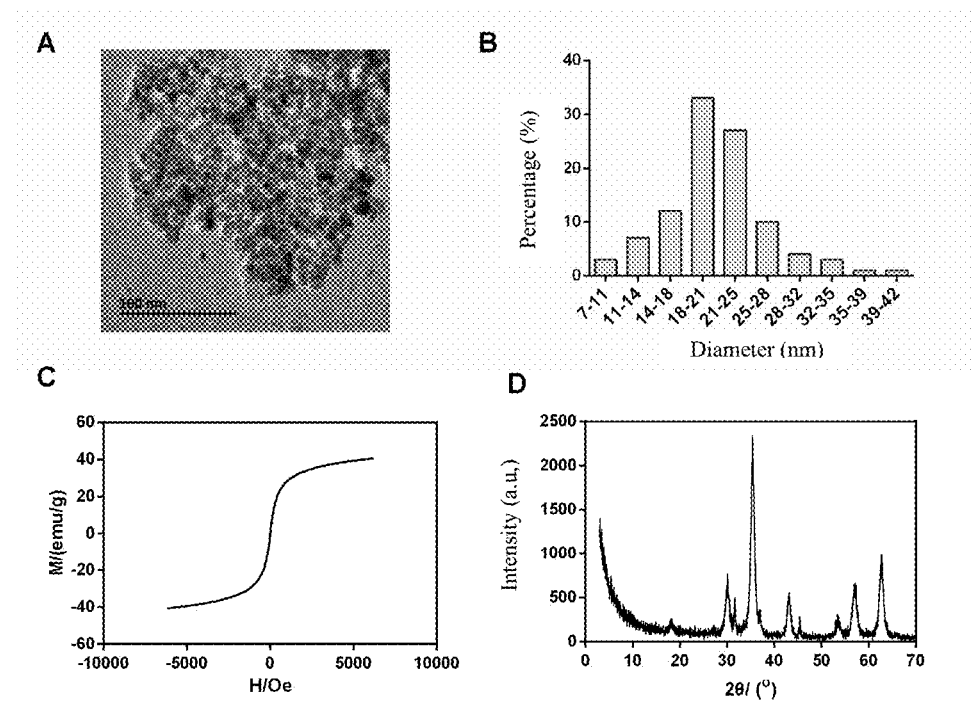
FIG. 2. (A) Transmission electron microscopy (TEM) micrograph, (B) TEM particle size statistics, (C) hysteresis curve and (D) X-ray diffraction (XRD) spectra of magnetic nanoparticles.

0.4970 g of $FeCl_2$ and 2.7030 g of $FeCl_3$ were mixed, and added with 25 ml NaOH (1.0 mol/L) dropwise. Ultrasonication was performed for 30 minutes by using an ultrasonic machine. The mixture was separated using a permanent magnet at the bottom. The supernatant was sucked and replaced with an equal volume of ultrapure water. It was repeated several times until pH=7 to obtain magnetic nanoparticles for further use. The magnetic nanoparticles were characterized by using TEM, hysteresis curve and XRD. The results are shown in FIG. 2. It can be seen from FIG. 2 that an average size of the magnetic nanoparticles was 20 nm, and the saturation magnetization values were 3.3-24.9 emu/g.

8 g of Cellulose was dissolved in 400 ml of an alkaline solution (prepared by dissolving 14 g of NaOH, 24 g of urea in 162 g of water). The mixture was mixed thoroughly and stored at 4° C. overnight to obtain a cellulose dispersion for further use. The magnetic nanoparticles and the cellulose dispersion were gently shaken and mixed for 10 minutes. The magnetic nanoparticles were captured with a permanent magnet over 5 minutes, and then washed with ultrapure water until pH=7 to obtain the cellulose magnetic nanoparticles.

Example 3

The main object of the example is to evaluate cellulose coating on surfaces of cellulose magnetic nanoparticles.

Figure 3:
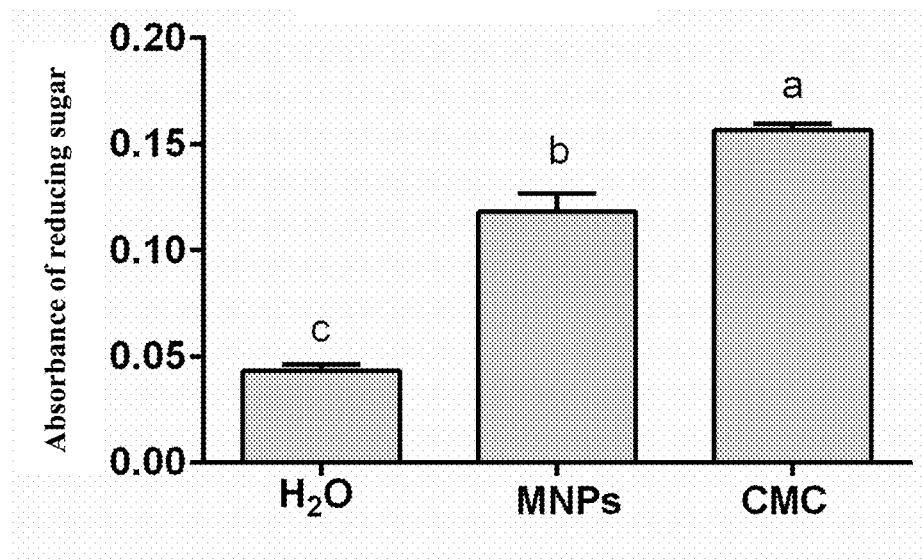
FIG. 3. Graph of quantitative evaluation of cellulose coated on the surface of cellulose magnetic nanoparticles.

The cellulose magnetic nanoparticles were dissolved in the anaerobic diluent to prepare a solution of cellulose magnetic nanoparticles with a concentration of 17.4 mg/ml. 3 ml of The above-mentioned cellulose magnetic nanoparticle solution, water (negative control) and sodium carboxymethyl cellulose (positive control, 5 mg/ml) each were added to 1 ml of cellulase solution (1 mg/ml), placed in a water bath at 50° ° C. for 30 min, and then in a boiling water bath for 10 min. After cooled to room temperature, each of the solutions was added to 3 ml of DNS solution, and placed in a boiling water bath for 10 min. After cooled to room temperature, all of the solutions were adjusted to 25 ml. OD values were measured at a wavelength of 550 nm using a spectrophotometer. The results are shown in FIG. 3. It can be seen from FIG. 3 that after cellulase treatment, reducing sugars were released from the cellulose magnetic nanoparticles. It indicated that the surfaces of magnetic nanoparticles were successfully coated with cellulose.

Example 4

The main object of the present example is to obtain optimal concentrations of cellulose magnetic nanoparticles binding to bacteria, and bacterial capture efficiency.

Figure 4:
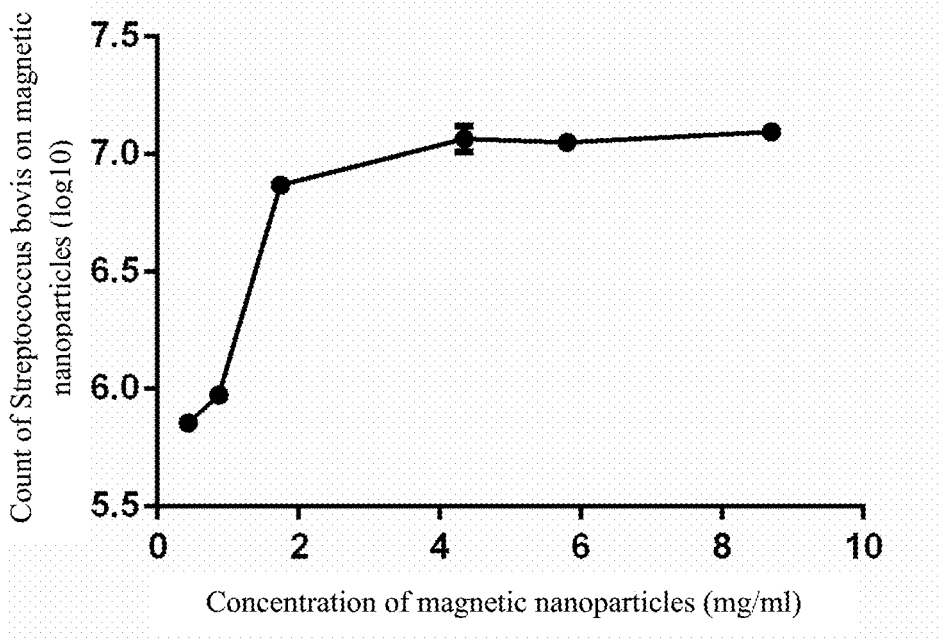
FIG. 4. Graph of evaluation of the binding ratios and efficiency of cellulose magnetic nanoparticles to bacteria.

The cellulose magnetic nanoparticles were dissolved in the anaerobic diluents to prepare solutions, which were diluted to a concentration of cellulose magnetic nanoparticles of 8.70 mg/mL, 5.80 mg/mL, 4.35 mg/mL, 1.74 mg/mL, 0.87 mg/mL, 0.44 mg/mL, respectively. The volume ratios of the diluted solutions to *Streptococcus bovis* ($1.0 \times 10^8$ CFU/mL) were 5:5 (the total volumes were 1 mL). After the mixtures were mixed for 10 minutes and allowed to stand, the cellulose magnetic nanoparticles were captured by a magnet, and the liquid was discarded. The bacterial DNA adhered to cellulose magnetic nanoparticles was extracted using Bacterial genomic DNA extraction kits (purchased from Tiangen Biochemical Technology Co., Ltd.) to quantify *Streptococcus bovis*, and determine the efficiency of cellulose magnetic nanoparticles binding to bacteria. The results are shown in FIG. 4. It can be seen from FIG. 4 that as concentrations of cellulose magnetic nanoparticles increased, the amounts of *Streptococcus bovis* adhered increased. The concentration of cellulose magnetic nanoparticles was at least 4.35 mg/ml. When the concentration of cellulose magnetic nanoparticles was 8.7 mg/ml, the bacterial binding efficiency achieved 99%.

Example 5

The main object of the example is to evaluate long-term binding stability between cellulose magnetic nanoparticles and bacteria.

Figure 5:
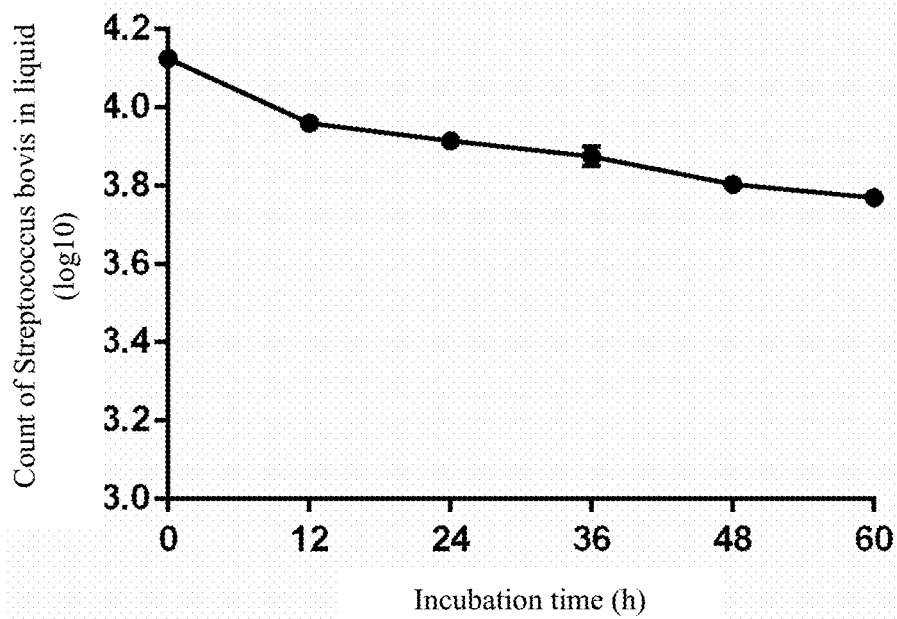
FIG. 5. Graph showing the binding stability between cellulose magnetic nanoparticles and bacteria.

The cellulose magnetic nanoparticles were dissolved in the anaerobic diluent to prepare a cellulose magnetic nanoparticle solution with a concentration of 8.70 mg/ml. 0.5 mL of the above-mentioned cellulose magnetic nanoparticle solution was mixed with 0.5 mL of *Streptococcus bovis* ($1.0 \times 10^8$ CFU/mL). After the mixture was mixed thoroughly for 10 minutes, the cellulose magnetic nanoparticles were captured by a magnet, the supernatant was sucked, and an equal volume of the anaerobic diluent was added. After the cellulose magnetic nanoparticles were washed twice, the anaerobic diluent was added. The mixture was incubated at 4° C. for 0 h, 12 h, 24 h, 36 h, 48 h, 60 h, respectively. The cellulose magnetic nanoparticles were captured by a magnet. DNA was extracted from the suspension and *Streptococcus bovis* was quantified by qPCR. The results are shown in FIG. 5. It can be seen from FIG. 5 that with the increase of incubation time, *Streptococcus bovis* had a tendency to fall off from the surface of the cellulose magnetic nanoparticles. After 60 hours of incubation, 9.76% of *Streptococcus bovis* dissociated from the cellulose magnetic nanoparticles.

Example 6

The main object of the example is to evaluate specificity of cellulose magnetic nanoparticle in isolation.

Figure 6:
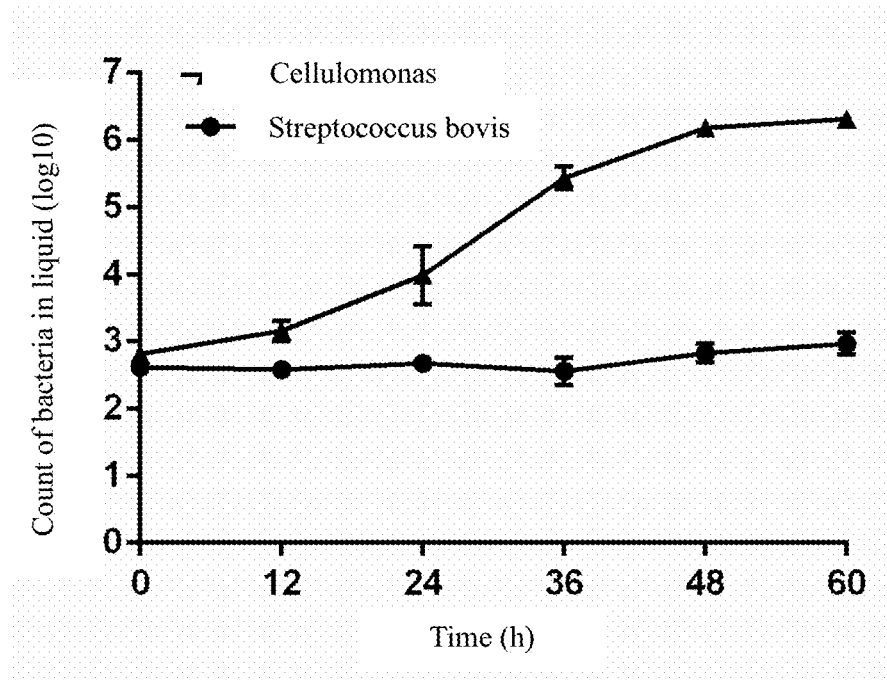
FIG. 6. Graph of evaluation of the specificity of cellulose magnetic nanoparticles binding to anaerobic cellulolytic bacteria.

The cellulose magnetic nanoparticles were dissolved in the anaerobic diluent to prepare a solution. After *Streptococcus bovis* and Cellulomonas were mixed in equal volumes, 0.5 mL of the mixture and 0.5 mL of the cellulose magnetic nanoparticle solution were mixed. After the mixture was mixed thoroughly for 10 minutes, the cellulose magnetic nanoparticles were captured by a magnet, the supernatant was discarded, and replaced with an equal volume of the anaerobic diluent. Such operation was repeated twice. The mixture was incubated at 30° C. for 0 h, 12 h, 24 h, 36 h, 48 h, 60 h, respectively. DNA was extracted from the suspension. *Streptococcus bovis* (non-cellulolytic bacterium) and Cellulomonas (cellulolytic bacterium) were quantified by qPCR. The results are shown in FIG. 6. It can be seen from FIG. 6 that with the increase of incubation time, Cellulomonas (cellulolytic bacterium) gradually dissociated from the surface of the cellulose magnetic nanoparticles into the solution, *Streptococcus bovis* (non-cellulolytic bacterium) basically did not dissociate. The efficiency of specific isolation of cellulolytic bacteria was 99.95%.

The above-mentioned products were extracted using Bacterial genomic DNA extraction kits (purchased from Tiangen Biochemical Technology Co., Ltd.).

The extracted bacterial genomes were quantified by qPCR using designed primers.

| Species | Primer sequence(5'-3') | Amplified fragment length (bp) | Annealing Temperature (° C.) Tm |
|---|---|---|---|
| *Streptococcus bovis* | F: TTCCTAGAGATAG GAAGTTTCTTCGG R: ATGATGGCAACT AACAATAGGGGT | 128 | 55 |
| *Cellulomonas* | F: SCCGCAAGGCTAA AACYCAAAGAAA R: CAWRACSYGCTGGC AACATRGGACG | 120 | 58 | qPCR System:

| | |
|---|---|
| Forward primer | 1 |
| Reverse primer | 1 |
| TB Green Premix Ex Taq II (Tli RNaseH Plus) (2×) | 12.5 |
| Template DNA | 2 |
| Sterile water | 8.5 |
| Total volume | 25 μL |

The qPCR reaction procedure was as follows: pre-denaturation at 95° C. for 30 s, 95° C. for 5 s, 60° C. for 30 s, 72° C. for 34 s, 40 cycles.

It can be seen from the above examples 3-6 that in terms of coating, the surfaces of magnetic nanoparticles were successfully coated with cellulose; in terms of binding ratio, when the bacterial concentration was $1.0 \times 10^8$ CFU/mL, the concentration of cellulose magnetic nanoparticles should be adjusted to 8.7 mg/mL, and the bacterial binding efficiency achieved 99%; in terms of stability, when the bacteria were stably adhered to the cellulose magnetic nanoparticles for 60 h, the stability was up to 90.24%, therefore the incubation time was preferably not more than 60 h; in terms of specificity, the efficiency of specific isolation of anaerobic cellulolytic bacteria was 99.95%.

The above-mentioned examples are preferred embodiments of the present invention, but the embodiments of the present invention are not limited to the above-mentioned examples. Any other alteration, modification, substitution, combination, simplification, etc., made without departing from the spiritual essence and principle of the present invention is equivalent replacement and falls within the scope of protection of the present invention.

The invention claimed is:

1. A method for separating anaerobic cellulolytic bacteria and anaerobic non-cellulolytic bacteria, comprising:
   mixing bacteria and cellulose magnetic nanoparticles in a first solution, wherein the bacteria comprises anaerobic cellulolytic bacteria and anaerobic non-cellulolytic bacteria, and each cellulose magnetic nanoparticle comprises cellulose coated on a surface of a magnetic nanoparticle, and anaerobic cellulolytic bacteria and anaerobic non-cellulolytic bacteria adhere to the cellulose coated on the magnetic nanoparticles;
   separating the cellulose magnetic nanoparticles from the first solution using magnetic attraction;
   incubating the cellulose magnetic nanoparticles in a second solution for a period of time, wherein cellulose having anaerobic cellulolytic bacteria adhered thereto degrades and releases anaerobic cellulolytic bacteria into the second solution, and the anaerobic non-cellulolytic bacteria remains adhered to the cellulose magnetic nanoparticles; and
   separating the cellulose magnetic nanoparticles from the second solution using magnetic attraction to obtain a second solution enriched in anaerobic cellulolytic bacteria.

2. The method according to claim 1, wherein the magnetic nanoparticles are selected from $Fe_3O_4$ nanoparticles.

3. The method according to claim 1, wherein the first solution is formulated by adding cellulose magnetic nanoparticles into an anaerobic diluent.

4. The method according to claim 1, further comprising:
   (1) dispersing cellulose in an alkaline solution to obtain a cellulose dispersion;
   (2) mixing and reacting magnetic nanoparticles and the cellulose dispersion to obtain the cellulose magnetic nanoparticles.

5. The method of preparation according to claim 4, wherein a concentration of the cellulose magnetic nanoparticles in the cellulose dispersion is from 7 mg/mL to 28 mg/mL.

6. The method of preparation according to claim 4, wherein the magnetic nanoparticles comprises $FeCl_2$ and $FeCl_3$ and step (2) is carried out under ultrasonication.

7. The method of preparation according to claim 4, wherein the alkaline solution in the cellulose dispersion is sodium hydroxide, urea, or a mixture thereof.

8. The method of preparation according to claim 4, wherein step (2) is carried out at, a reaction temperature is room temperature for a time of 5 minutes to 15 minutes.

9. The method according to claim 1, wherein the average particle size of the magnetic nanoparticles is from 10 nm to 30 nm.

10. The method according to claim 1, wherein a concentration of the cellulose magnetic nanoparticles is from 0.1 mg/ml to 10 mg/ml.

11. The method according to claim 1, wherein a concentration of the bacteria in the first solution is $0.8 \times 10^8$ CFU/mL to $1.2 \times 10^8$ CFU/mL.

12. The method according to claim 1, wherein the incubating time is from 5 minutes to 60 hours.

* * * * *